United States Patent [19]

Bannert

[11] Patent Number: 5,147,648

[45] Date of Patent: Sep. 15, 1992

[54] METHOD OF IMPROVING THE ADHESIVENESS OF GELS TO MUCOSAE

[76] Inventor: Christian Bannert, Miltenbergstrasse 17, D-8900 Augsburg, Fed. Rep. of Germany

[21] Appl. No.: 584,373

[22] Filed: Sep. 17, 1990

Related U.S. Application Data

[63] Continuation of Ser. No. 272,801, filed as PCT/EP86/00750, Dec. 15, 1986.

[30] Foreign Application Priority Data

Jan. 16, 1986 [DE] Fed. Rep. of Germany ....... 3601132

[51] Int. Cl.$^5$ .......................... A61K 9/12; A61K 33/00
[52] U.S. Cl. ...................................... 424/435; 424/434
[58] Field of Search ....................... 424/434, 435, 436

[56] References Cited

U.S. PATENT DOCUMENTS 4,572,832 2/1986 Kigasawa et al. .................. 424/435

FOREIGN PATENT DOCUMENTS 670837 10/1965 Belgium .
0048123 3/1982 European Pat. Off. .
2224700 12/1972 Fed. Rep. of Germany .
60-116630 6/1985 Japan .................................. 424/435

Primary Examiner—Thurman K. Page
Assistant Examiner—Peter F. Kulkosky
Attorney, Agent, or Firm—Felfe & Lynch

[57] ABSTRACT

For improving the adherence of gels to the mucous membranes, one applies separately to the same area of a mucous membrane two components capable of forming together a gel, for example a metallic salt and at least one polysaccharide. This gel is useful as carrier for medicaments.

4 Claims, No Drawings

METHOD OF IMPROVING THE ADHESIVENESS OF GELS TO MUCOSAE

This application is a continuation, of application Ser. No. 272,801, filed as PCT/EP86/00750, Dec. 15, 1986, now pending.

DESCRIPTION

The invention has to do with a method of improving the adhesiveness of gels to mucosae and with an appropriate agent for this method.

It has proved useful to treat diseases of the mucosa with gels. On the one hand they can be used to protect the mucosa and keep it moist. On the other hand they are used to apply disinfectants and medication to the mucosa and allow them to take effect. These gels—which are produced from synthetic or phytogenic components and which can contain various active substances—are applied to the mucosa in the nose, mouth, throat and urogenital areas and in the gastro-instestinal tract.

Thus, for instance, it is known from DE-OS 31 52 319 as well as EU-A1 0 059 221 that water-soluble alginates in the form of a gel can be used to stop hemorrhages in the gastrointestinal tract. But the disadvantage to these known substances is that they adhere poorly to mucosae and do not stay very long on the spot where they are applied and are supposed to take effect. They bead on the mucosa and are unable to bring about the desired effect.

Moreover, it is known from DE-OS 22 24 700 to produce a film from a water-insoluble metal salt of a film-forming material, such as alginic acid. Discs or small pieces can then be cut out of the so produced film and then put on wounds. Here, too, the drawback occurs that the put-on pieces of film slip because they do not adhere to the mucosa. Further, it is known from BE-PS 670 837, to apply to the skin a film from a water-insoluble salt of alginic acid, for therapeutic and cosmetic purposes. Here, first a solution of alginic acid with a viscosity sufficient for adhesion to the skin is applied to this skin. Subsequently, a calcium salt solution is applied to this film in order to thus coagulate the insoluble calcium alginate. In this manner, a purely mechanically working protective bandage is applied to the skin. In this manner it is not possible either to apply to the mucosa a film which adheres well.

The object of the present invention was to prevent these known disadvantages and to arrive at a process which would improve the adhesiveness of gels to mucosae.

This objective is achieved by a process for improving the adhesiveness of gels to mucosae, which process is characterized in that a solution containing a metal salt which together with a polysaccharide is capable of forming a gel is first applied to an area of mucosa and subsequently the solution containing the polysaccharide capable of forming a gel is applied to the same area.

Instead of using a finished gel, components which together are capable of forming a gel were applied to the mucosa. Surprisingly, it was seen that good adhesiveness could be obtained from the gel which subsequently formed.

The two components capable of forming a gel are dissolved separately. The solutions are then applied one after the other. Application can be carried out in the usual way. It is preferable that the two components be sprayed onto the mucosa, that they be applied to the appropriate area via probe or catheter, or that application take place by drinking the two solutions.

As components capable of forming a gel there can be used metal salts and polysaccharides which lead to gel formation when mixed together. In addition, they must be mucosa-tolerable and non-toxic. Combinations of alginic acid, polyguluronic acid, polymannuronic acid, propyleneglycol alginic acid, polygalacturonic acid, their salts, or esters and their mixtures as well as pectins with pharmaceutically tolerable metal salts are, for instance, appropriate.

For the components capable of forming a gel, calcium salts together with alginic acid or one of its derivatives, or with a pectin with a low degree of esterfication are preferable. Calcium salts react with alginic acid and pectins and their derivatives and form cross-linkings. As the metal salt concentration is increased, viscosity also increases, and then gel formation occurs. For the metal salt, the use of calcium salts is preferred, whereby all pharmaceutically tolerable salts—like calcium salts with organic anions like citrate, lactate, aspartate, saccharate, oxovalerate, gluconate, lactobionate and lactogluconate - can be used as calcium salts. The use of calcium gluconate is preferable.

For the alginic acid derivative, sodium alginate is preferable; its whole range of viscosity can be used. Viscosity is classified according to the 1% solution. Measurements are taken at 25 degrees C. with a Brookfield-Viscosimeter. Standard marketed alginate types are:

very low viscose sodium alginate: (5 cps),
low viscose sodium alginate: (50 cps),
high viscose sodium alginate: (400 cps),
very high viscose sodium alginate: (1,350 cps).

In addition to alginic acid, there are other mono- and poly-saccharides in brown algae. Important for mucosae are the fucose and the ester sulfates. By using the appropriate methods to prepare the brown algae, mixtures consisting of alginates, fucose and estersulfates can be obtained. These mixtures are also appropriate for components used in the gel formation in the inventive procedure under discussion.

For a pectin, one with a low degree of esterfication is preferable. Polygalacturonic acids, for instance, with a concentration of about 37 to 39% methoxylized carboxylate groups.

The two components are used in solution. Here it is preferable that the metal salt be used in a concentration of 0.1 to 50 mMol metal/100 ml and the polysaccharide in a concentration of 0.1 to 12.5 weight %. The respective concentration can be easily determined. It is also dependent on the degree of viscosity of the polysaccharide which is used.

Pharmaceutically tolerable agents which dissolve the respective components well are used as solvents. The use of distilled water provided with a pharmaceutically tolerable preservative is preferable.

The gel which is formed in accordance with the invention under discussion can be used to keep the mucosa moist or to protect it. In addition, a disinfectant and/or drugs can be applied to the mucosa in another formulation with one of the components used in accordance with the invention. The gel which, according to the invention, forms on the mucosa can then be used in treating diseases which affect mucosae.

The gels which are obtained by the procedure in accordance with the invention under discussion are preferably used as carrier material for a drug. Here the drug, in the applicable dose, is introduced into one of the two component solutions and then both components are applied to the mucosa.

A further aspect of the invention is an agent which adheres well to mucosae and which is characterized by its containing at least two components, physically separate, which together are capable of forming a gel.

The agent obtained in accordance with the invention allows for the facile formation of gels on mucosae with long-lasting and durable adhesiveness.

At least one metal salt and at least one polysaccharide are used for the components—physically separate from one another—of the agent in accordance with the invention. The application of a calcium salt is preferable for the metal salt, and special preference is given to the use of an organic calcium salt. The use of alginic acid, polyguluronic acid, polymannuronic acid, propyleneglycol alginic acid, polygalacturonic acid, their salts, or esters as well as pectins—especially with a low degree of esterification—and their mixtures are preferable for the polysaccharide.

It is preferable that both components be dissolved in water. It is preferable that one solution contain 0.1 to 50 mMol metal/100 ml, and that the other solution contain 0.1 to 12.5 weight % of at least one polysaccharide.

In a preferred formulation, at least one of the two components of the agent in accordance with the invention contains additional drugs, disinfectants, humectants and/or preservatives or other customary additives. Thus, for instance, to increase the flexibility of the gel, sorbite or glycerine is added. Furthermore, it may be appropriate to add tensides so as to improve wetting.

The concentration of the two components of the agent in accordance with the invention is generally about the same in both. But in special cases it can be advantageous to introduce one of the two solutions with a higher concentration and slighter volume. The concentration can also influence the kind of gel which is to be formed. Thus, for instance, solutions with lower concentrations of alginate or pectin on the one hand, and metal salt on the other, form thin gel films, while the introduction of the components in higher concentrations result in sturdy gel films.

Thin gel films are especially suited for saliva substitutes in the mouth and throat areas, and as artificial nasal secretion in the nose. These thin gel films can be obtained, for instance, by using the same volumes of a calcium salt solution and a sodium alginate solution, whereby concentrations of 0.1 to 7 mMol calcium/100 ml. and 0.1 to 5 weight-% natrium alginate are used. Here one first sprays on the calcium salt solution, then the alginate solution. For the mucosa of the esophagus, which cannot be reached by spraying, the best procedure for application is drinking the two component solutions. For the gastro-intestinal area application takes place via probe or catheter.

If solutions with higher concentrations are used, more solid gel layers are produced. In this case, too, first the metal salt component and then the polysaccharide component is applied.

Of the two dissolved components, the metal salt solution—especially when present in higher concentrations—has a lower viscosity. This low-viscose solution can make its way into the creases and irregularities of the mucosa. When the higher viscose polysaccharide solution is then added, gel formation also occurs in the creases and irregularities of the mucosa and for this reason adhesiveness is very good. These solid gel films cover the damaged mucosa and protect it from gastric acid, enzymes, bacteria or other harmful influences from outside. Given the procedure in accordance with the invention under discussion, a solid gel film can be introduced to a specifically desired spot—for instance via probe or catheter—by applying the two components to, or by dripping or pouring them onto, the desired spot. This sort of application is well—-suited for, among others, diseases of the mucosa which are caused by reflux esophagitis, ulcers following sclerosation in the esophagus, gastric ulcers, Crohn's disease and radiation ulcers in the large intestine.

The especially adhesive gels obtained by the procedure in accordance with the invention under discussion are especially suited for use as a carrier material for drugs or disinfectants. Using the gels obtained in accordance with the invention under discussion, drugs and disinfectants can be applied locally with great accuracy.

The following examples serve to elucidate the invention: unless otherwise stated, all percentages refer to weight.

EXAMPLE 1

An agent for the protection of mucosae was produced. For this purpose a solution containing calcium gluconate in a concentration of 0.5% in distilled water was prepared. A preservative was added to this solution. A solution containing 0.5% sodium alginate in distilled water was also prepared. A preservative was also added to this solution. The two solutions were sprayed onto the mucosa. A gel formed which illustrated long-lasting adhesiveness.

EXAMPLE 2

An agent for the disinfection of mucosae was produced. For this purpose 0.5 weight % calcium gluconate was dissolved in distilled water. Preservatives were added. 0.5 weight % sodium alginate and 0.2 weight % 4-chloro-3-methylphenol were dissolved in distilled water. Both solutions were sprayed onto the mucosa at the same time. A gel formed which adhered to the mucosa.

EXAMPLE 3

An agent which can be used as artificial saliva in the throat area was produced. The two components were comprised of the following:

| Solution A | | Solution B | |
|---|---|---|---|
| calcium gluconate | 0.5% | sodium alginate, high viscose | 0.75% |
| sodium chloride | 0.1% | | |
| potassium chloride | 0.2% | sodium chloride | 0.1% |
| sorbite | 0.2% | potassium chloride | 0.2% |
| water ad | 100 ml | sorbite | 0.2% |
| | | water ad | 100 ml |

EXAMPLE 4

An agent which can be used as artificial saliva was produced. It was comrpised of the following:

| Solution A | | Solution B | |
|---|---|---|---|
| calcium gluconate | 1% | sodium alginate, low viscose | 1% |
| water ad | 100 ml | pectin | 0.2% |
| | | water ad | 100 ml |

EXAMPLE 5

An agent like that in Example 3 was produced. To improve wetting, a tenside was added. The agent was comprised of the following:

| Solution A | | Solution B | |
|---|---|---|---|
| calcium gluconate | 0.5% | sodium alginate, low viscose | 0.75% |
| cremophore EL (tenside) | 0.025% | water ad | 100 ml |
| sorbite | 1% | | |
| water ad | 100 ml | | |

EXAMPLE 6

An agent suitable for artificial saliva was produced. It was comprised of the following:

| Solution A | | Solution B | |
|---|---|---|---|
| calcium gluconate | 3% | sodium alginate, very high viscose | 0.1% |
| sorbite | 5% | | |
| water ad | 100 ml | sorbite | 5% |
| | | water ad | 100 ml |

EXAMPLE 7

An agent was produced which serves as a carrier substance for neuraminic acid as the active substance:

| Solution A | | Solution B | |
|---|---|---|---|
| calcium gluconate | 0.1% | sodium alginate, very low viscose | 5% |
| water ad | 100 ml | | |
| | | neuraminic acid | 0.1% |
| | | water ad | 100 ml |

EXAMPLE 8

An agent was produced which can be used as artificial nasal secretion and sprayed directly into the nose:

| Solution A | | Solution B | |
|---|---|---|---|
| calcium gluconate | 0.5% | sodium alginate, low viscose | 1.5% |
| sodium chloride | 0.75% | | |
| potassium chloride | 0.13% | sodium chloride | 0.75% |
| sorbite | 0.5% | potassium chloride | 0.13% |
| water ad | 100 ml | sorbite | 0.5% |
| | | water ad | 100 ml |

EXAMPLE 9

The following agent was produced to keep the nasal mucosae moist:

| Solution A | | Solution B | |
|---|---|---|---|
| calcium gluconate | 0.75% | sodium alginate, low viscose | 2% |
| sodium chloride | 1.5% | | |
| potassium chloride | 0.23% | sodium chloride | 1.5% |
| sorbite | 0.5% | potassium chloride | 0.23% |
| water ad | 100 ml | sorbite | 0.5% |
| | | water ad | 100 ml |

EXAMPLE 10

An agent was produced for use as artificial nasal secretion:

| Solution A | | Solution B | |
|---|---|---|---|
| calcium gluconate | 2% | sodium alginate, low viscose | 1% |
| sorbite | 5% | water ad | 100 ml |
| water ad | 100 ml | | |

EXAMPLE 11

An agent was produced that was used to apply xylometazoline as a vasoconstrictor to nasal mucosae:

| Solution A | | Solution B | |
|---|---|---|---|
| calcium gluconate | 0.5% | sodium alginate, low viscose | 1.5% |
| sodium chloride | 0.75% | | |
| potassium chloride | 0.13% | sodium chloride | 0.75% |
| sorbite | 0.5% | potassium chloride | 0.13% |
| xylometazoline | 0.1% | sorbite | 0.5% |
| water ad | 100 ml | water ad | 100 ml |

EXAMPLE 12

An agent was produced which serves to protect mucosae:

| Solution A | | Solution B | |
|---|---|---|---|
| calcium gluconate | 1% | pectin | 1% |
| water ad | 100 ml | water ad | 100 ml |

EXAMPLE 13

An agent was produced which was used to apply neuraminic acid to nasal mucosae:

| Solution A | | Solution B | |
|---|---|---|---|
| calcium gluconate | 0.1% | sodium alginate, very low viscose | 5% |
| water ad | 100 ml | | |
| | | neuraminic acid | 0.1% |
| | | water ad | 100 ml |

I claim:

1. The method of treating xerostomia with a gel having an improved adhesiveness to the oral mucosa of a human patient, which comprises first applying to the oral mucosa of said patient an aqueous solution of a calcium salt which is capable of forming a gel with a polysaccharide, where the calcium salt solution has a concentration of 0.01 to 50 mMols of calcium per 100 ml, and subsequently applying to the thus treated oral mucosa of said patient an aqueous solution of a polysaccharide selected from the group consisting of sodium alginate and pectin, where said polysaccharide solution contains 0.01 to 12.5% by weight of polysaccharide.

2. The method of claim 1, wherein said calcium salt is calcium chloride and said polysaccharide is pectin.

3. The method of claim 1, wherein said calcium salt is calcium gluconate and said polysaccharide is sodium alginate.

4. The method of claim 1, wherein the calcium salt solution and the polysaccharide solution are sequentially applied to the mucosa of the mouth by spraying or rinsing.

* * * * *